United States Patent [19]
Csakvary et al.

[11] 3,983,368
[45] Sept. 28, 1976

[54] APPARATUS FOR NON-TRAUMATIC DETERMINATION OF THE MASS AND THE POSITION OF THE CENTER OF GRAVITY OF A BODY

[75] Inventors: Etienne Csakvary, Maurepas; André Pascal, Palaiseau, both of France

[73] Assignee: Commissariat a l'Energie Atomique, Paris, France

[22] Filed: Mar. 13, 1974

[21] Appl. No.: 450,564

[30] Foreign Application Priority Data
Mar. 19, 1973   France .............................. 73.09762

[52] U.S. Cl. .............................. 235/151.3; 250/366; 250/367
[51] Int. Cl.² .......................................... G01T 1/20
[58] Field of Search .................. 235/151.3; 250/312, 250/358, 359, 360, 313, 320, 321, 323, 490, 491, 366–369, 361–363; 73/65; 356/157, 158

[56] References Cited
UNITED STATES PATENTS

| | | |
|---|---|---|
| 3,489,901 | 1/1970 | Brown ............................ 250/358 X |
| 3,673,394 | 6/1972 | Hartmann ....................... 235/151.3 |
| 3,778,614 | 12/1973 | Hounsfield ......................... 250/362 |
| 3,784,820 | 1/1974 | Miraldi ............................... 250/362 |
| 3,808,440 | 4/1974 | Petit-Clerc ..................... 250/366 X |
| 3,809,886 | 5/1974 | Cochran et al. ................ 250/491 X |
| 3,809,904 | 5/1974 | Clarke et al. ....................... 250/358 |
| 3,852,601 | 12/1974 | Casale ................................ 250/366 |
| 3,854,047 | 12/1974 | Suhami et al. ..................... 250/366 |
| 3,870,886 | 3/1975 | Casale ................................ 250/367 |

*Primary Examiner*—Edward J. Wise
*Attorney, Agent, or Firm*—William R. Woodard

[57] ABSTRACT

A line body portion is subjected to a beam z or parallel beams of electromagnetic radiation having transverse dimensions which are smaller than those of the body portion. The beam is displaced in space in order to sweep the entire volume of the body portion and the attenuation resulting from the passage of the beam through the body is measured in respect of each position of the beam. The mass of the unitary volume of the body portion traversed by the beam is deduced from the measurement, the total mass thereof and the position of its center of gravity being then calculated from a knowledge of the mass of each unitary volume.

3 Claims, 4 Drawing Figures

APPARATUS FOR NON-TRAUMATIC DETERMINATION OF THE MASS AND THE POSITION OF THE CENTER OF GRAVITY OF A BODY

This invention relates to apparatus for determination of the mass and position of the center of gravity of an object. The invention finds an application in mechanics and in physiology in which determination of the mass and the center of gravity of body segments attached to an articulation is essential to the study of articular physiology.

Estimation of the mass and the position of the center of gravity of an object as performed by known methods of weighing or computation are inapplicable in many cases, especially when the part to be studied is of complex shape or when a part of the human body is involved. The precise aim of this invention is to provide a method and a device which are not attended by these disadvantages and which are also applicable to objects of any shape and character. Since the method is atraumatic, it can be employed in physiology without having any harmful effect on the patient.

SUMMARY OF THE INVENTION

Briefly, a device for determining the mass and the position of the center of gravity of a body or body portion comprises:

- at least one source of electromagnetic radiation which emits a beam or parallel beams and a corresponding number of detectors which serve to detect said radiation and each receives one of said beams,
- a support, rigidly fixed to said sources and said detectors, movable with respect to the body,
- a system for determining the coordinates of the sources with respect to three mutually intersecting reference axes, first calculating means for calculating the logarithm of the ratio between the intensity $I_0$ received by each detector when this latter is in direct view of the source and the intensity $I$ received by the same detector when the body is interposed between the source and the detector and, second calculating means responsive to the first calculating means and to the coordinate determining system for calculating the coordinates of the center of gravity of the body.

In one particular form of construction, the device according to the invention is characterized in that the movable support is a rigid frame on which are fixed two sources and two detectors located opposite to said sources, the beam emitted by one source being perpendicular to the beam emitted by the other source, said movable support being capable of displacement in the two directions parallel to said beams and in a third direction at right angles to the plane of said two beams.

The absorption of an electromagnetic radiation by material is a function of the mass $m$ traversed by the beam. If $I_0$ designates the incident flux, $I$ designates the emergent flux from the irradiated object, $a$ designates the mass absorption coefficient of the material traversed and $m$ designates the mass of the object traversed, we have:

$$I = I_0 \exp(-am) \qquad (1)$$

from which the mass traversed by the beam may be derived if the absorption coefficient $a$ is known. We have:

$$m = (1/a) \log (I_0/I) \qquad (2)$$

In accordance with the method of the invention, the object to be studied is swept by a beam of electromagnetic radiation, especially gamma or X radiation. By measuring the attenuation sustained by said beam as it passes through the body, it is possible to determine the value of the mass which is traversed. If the cross-section of the sweeping beam has much smaller dimensions than those of the object, it is thus possible to determine a series of partial masses of the object corresponding to different volumes swept by the beam and these volumes will be designated hereinafter as "unitary volumes". A knowledge of the mass of each unitary volume makes it possible by means of a summation to determine the total mass of the object and to find the position of the center of gravity by means of a simple calculation.

If a space is related to three rectangular axes $Ox$, $Oy$, $Oz$, it is convenient for the formulation of the problem to employ a beam for sweeping in a direction parallel to one of said axes, for example a direction parallel to the axis $Oy$. The position of said beam in space is then wholly defined by its projection in the plane $xOz$, that is to say by two coordinates $x$ and $z$. It is further postulated that the transverse cross-section of said beam has the dimensions $dx$ and $dz$. This does not necessarily mean that the beam has a rectangular transverse cross-section or that its dimensions are infinitely small, since a beam of medium dimensions is in fact employed. It would clearly be possible in practice, however, to produce a beam having a rectangular cross-section by suitably stopping-down the beam which is emitted by the radiation sources.

Determination of the absorption in the unitary volume traversed by the beam makes it possible with the aid of the formula (2) given above to determine the mass $M(x,z).dx.dz$ of the corresponding unitary volume. The total mass M of the object is deduced from a knowledge of this function by means of a double integration which is extended to all the values of $x$ and $z$:

$$M = \iint M(x,z).dx.dz \qquad (3)$$

If the product $x.M(x,z).dx.dz$ is calculated in respect of each value of the variables $x$ and $z$ and if this product is integrated in respect of all the possible values of the variables $x$ and $z$, the result of this integration divided by the total mass M of the object provides, as is well known, the abscissa X of the center of gravity of the object:

$$X = 1/M \iint x.M(x,z).dx.dz \qquad (4)$$

This is a first method of calculation of the abscissa of the center of gravity. It is possible, however, to employ another method which consists in splitting the double integration of formula (4) into a first integration in a plane having a predetermined coordinate $z$, and into a second integration on all the values assumed by the variable $z$. The first integration makes it possible to find the abscissa $x_g(z)$ of the center of gravity of the unitary segment having a thickness $dz$ and a coordinate $z$, said abscissa being given by the formula:

$$x_a(z) = \frac{\int_x x \cdot M(x,z) \cdot dx \cdot dz}{M(z) \cdot dz} \qquad (5)$$

where $M(z).dz$ is the mass of the unitary segment having a thickness $dz$ and a coordinate $z$ as obtained by integrating $M(x,z).dx.dz$ with respect to $x$.

A knowledge of the abscissa $x_a(z)$ of the center of gravity of the unitary segment having a coordinate $z$ makes it possible to find the abscissa X of the center of gravity of the total object by integration on all the values assumed by the variable $z$:

$$X = 1/M \int x_a(z).M(z).dz \qquad (6)$$

which naturally gives the small result as that obtained by the preceding method (relation 4).

In order to obtain the ordinate Y of the center of gravity of the object, one may proceed in the same manner with a beam which is directed parallel to the axis Ox, the projection of which in the plane yOz has the coordinates y and z. The calculation formulae for the ordinate Y are obtained from the formulae 4 and 6 given above by replacing the variable $x$ by the variable $y$.

A calculation of the coordinate Z of the center of gravity of the object is made either from the first beam which is parallel to Oy or from the second by means of operations which are wholly analogous to those which have just been specified. In the case in which the first beam is employed, Z is calculated by the first method as follows:

$$Z = 1/M \iint z.M(x,z).dx.dz$$

and by the second method as follows:

$$Z = 1/M \int z.M(z).dz$$

In practice, the displacement of the analytical beams may not be wholly continuous but may take place by means of a device which operates in step-by-step motion. Alternatively, the displacement may be continuous and the value of I is sampled periodically. In this case, it is apparent that all the foregoing operations remain valid except for the fact that the integration operations which presuppose continuous functions are replaced by summations on the samples which are obtained in respect of said functions when the variables assume a discrete series of values.

BRIEF DESCRIPTION OF THE DRAWINGS

The invention is further described by way of example with reference to the annexed drawings in which:

In FIG. 1, there is shown a general diagram of the device according to the invention which is assumed by way of explanation to make use of two analytical beams directed at right angles. In this figure, the space is related to three trirectangular axes Ox, Oy, Oz. The two analytical beams are generated by two sources $S_1$ and $S_2$. The transverse cross-section of the beam 1 emitted by the source $S_1$ has dimensions $dx$ and $dz$. The transverse cross-section of the beam 2 emitted by the source $S_2$ has dimensions $dy$ and $dz$. Two detectors $D_1$ and $D_2$ measure the intensity of the beams 1 and 2 which are transmitted through the object C in order to determine the mass and the coordinates of the center of gravity of said object. The sources $S_1$ and $S_2$ and the detectors $D_1$ and $D_2$ are mounted on a rigid frame 3, the plane of which is parallel to the plane $xOy$. The frame 3 is rigidly fixed to an arm 5 controlled by displacement means 4 of the type found in scintillographs of the kind used for medical radiography of a patient, in which a detector is carried movably in three dimensions on an overhanging horizontal arm that is itself movable vertically and on at least one horizontal axis, actuated in response to control means 6 of the kind used to control the arm of a scintillograph which makes it possible to displace the frame 3 along the three axes of coordinates Ox, Oy and Oz forming what may be called a "reference trihedron". The displacement means 6, as is normally provided in the case of the previously mentioned medical radiography equipment, also keeps track of the coordinates of the sources $S_1$ and $S_2$ with respect to the reference trihedron as the sources are displaced and accordingly generate electrical position output signals which are proportional to the values of $x$, $y$ and $z$.

Means for displacing a frame in three-co-ordinates are well known, being used in machine tools and the like, as well as in the scintillographs already referred to. A reversible motor operating linear, by rack-and-pinion, worm gear, or lead screw, for example, may be used for each of the coordinate axes, as is well known. FIG. 4 illustrates such a drive in one coordinate utilizing a rack-and-pinion conversion from rotary to linear motion. The drive for each of the three coordinate axes can all be basically the same.

Figure 1:
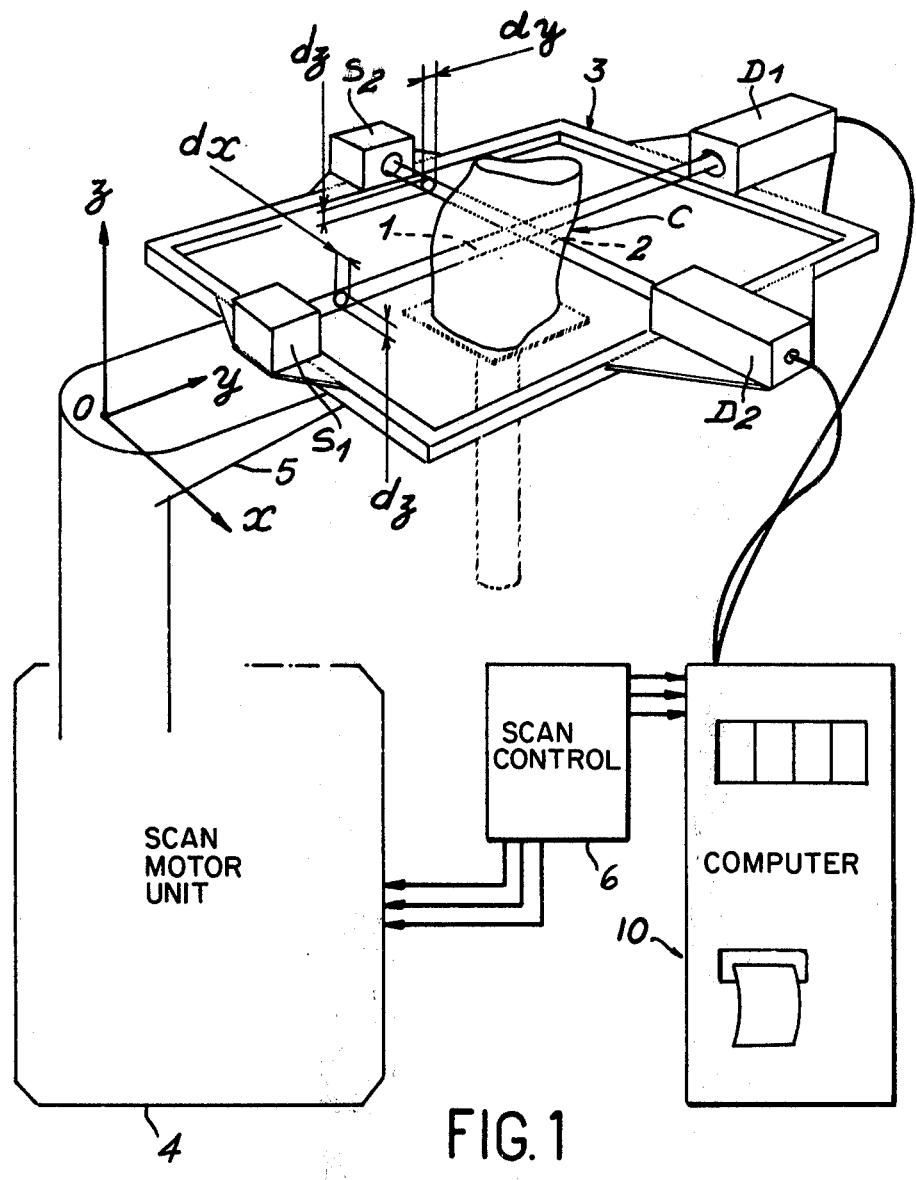
FIG. 1 is a diagrammatic perspective view of an apparatus in accordance with the invention utilizing two radiation sources and two detectors mounted on a universally movable arm for scanning a body portion.

A motor M powered by a voltage source S is mounted on the fixed base of the machine 4 and drives a rack R in either longitudinal direction (i.e. in either sense, in one co-ordinate), in accordance with a scanning movement that may be manually or automatically operated in any desired manner. The rack R for a first coordinate is affixed to a first movable support that moves, of course, only in the lengthwise direction of the rack. Then on that first movable support a second motor is mounted that drives another rack directed at right angles to the rack of the first coordinate drive and affixed to a second movable support, thus providing a second coordinate drive. The second movable support mounts a third motor that engages a rack at right angles to the lengthwise directions of the other two racks and affixed to the arm that carries the radiation sources and detectors. One of the three drives, of course, is vertical and the other two are horizontal. Each of the three drives includes a potentiometer P driven by the rack and energized by a d.c. voltage source (not shown) to produce a signal representative of the position of the rack relative to the immediately underlying support, hence of the position of the support arm in the coordinate direction defined by the rack in question.

The electrical position output signals are supplied to a computer 10 which also receives the electrical signals delivered by the detectors $D_1$ and $D_2$. The computer 10 processes the position signals delivered by the means 6 and the intensity signals delivered by the detectors $D_1$ and $D_2$ in order to calculate the masses of the unitary volumes through which the beams 1 and 2 pass and then to compute by means of the process defined earlier, the total mass of the object and the coordinates of its center of gravity.

Sweeping of the object C by the beams 1 and 2 can be carried out in several ways. In accordance with a first alternative procedure, the frame 3 is displaced in such a manner as to ensure that the beam 1 assumes all the possible values in $x$ and in $z$, and the calculations accordingly involve double integrals. Sweeping with the beam 2 is then repeated. In another alternative procedure, partial sweeps are carried out in a plane having a coordinate $z$ by displacing the frame 3 in translational motion parallel to Ox but by maintaining constant its coordinate $z$. When sweeping in $x$ has been completed, the frame is displaced in translational motion parallel to Oy while still maintaining the coordinate $z$. This makes it possible to calculate the coordinates $x_g(z)$, $y_g(z)$ and $z$ of the center of gravity of the unitary segment having a coordinate $z$ and a thickness $dz$. The frame 3 can clearly be translated in an oblique direction with respect to the axes Ox and Oy, thus resulting in simultaneous sweeping in $x$ and in $y$ and entailing the need to process in parallel the data derived from the two beams whereas, in the previous sweep, said data are processed sequentially, which reduces the number of circuits of the computer.

It is also possible to displace the sources and the detectors simultaneously on a stationary frame along the axes Ox and Oy and to impart to the frame $z$ solely a movement along Oz or even to carry out a displacement of the body to be studied.

Figure 2:
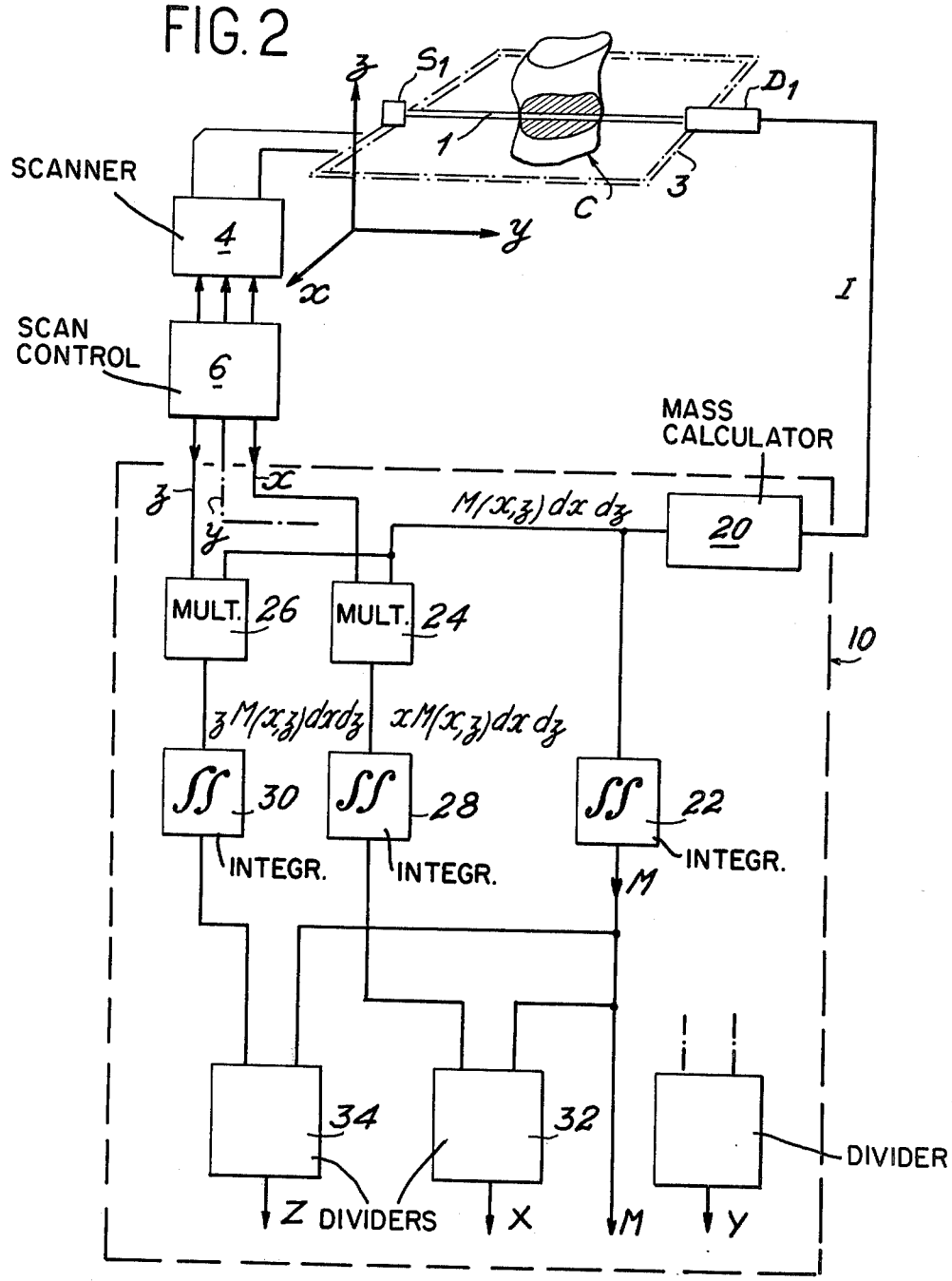
FIG. 2 is a block diagram of a circuit for making measurements with one of the detectors of the apparatus of FIG. 1, this being representative also of a corresponding circuit for use with the other detector.

Although anyone versed in the art can readily devise the structure of the computer 10 which serves to perform the operations of formulae (3) to (6), FIG. 2 indicates by way of explanation one possible schematic diagram of said computer in the case of the first alternative embodiment of the invention in which the coordinates of the center of gravity are calculated by means of formulae which are similar to the formula (4). With reference to FIG. 2, it is recalled that the object C to be studied is irradiated by a gamma-radiation beam 1 emitted by the source $S_1$. After passing through the object C, the intensity I of the beam is measured by the detector $D_1$. The position of the source $S_1$ is controlled by the means 6. The computer 10 receives the datum I from the detector $D_1$ and the data $x$ and $z$ of the coordinates of the source $S_1$ from the means 6.

On the basis of the three data I, $x$ and $z$, the computer 10 calculates the mass M of the object, the abscissa X and the coordinate Z of the center of gravity in the manner which will now be described. The signal I is processed in a stage 20 for calculation of the absorption in accordance with the formula (2) given in the foregoing. This stage delivers a signal which is proportional to the mass $M(x,z).dx.dz$ of the irradiated unitary volume. The double integration of this function within the integrator 22 serves to determine the mass M of the object. The multiplier 24 receives on the one hand the value of the mass of the unitary volume and on the other hand the coordinate $x$ which defines the position of the beam in the plane having the coordinate $z$. The multiplier 24 therefore forms the product $x.M(x,z).dx.dz$. Similarly, the multiplier 26 receives on the one hand the value of the mass of the unitary volume having the abscissa $x$ and the coordinate $z$ and on the other hand the value of said coordinate $z$. The multiplier 26 therefore forms a product $z.M(x,z).dx.dz$. The integrators 28 and 30 integrate these two products in respect of all the values of $x$ and $z$ assumed during the sweeping of the object C by the beam 1. The result of these double integrations is divided by the mass M of the object within the dividers 32 and 34, the outputs of which deliver respectively the abscissa X and the coordinate Z of the center of gravity of the object.

It is readily conceived that the second beam which is parallel to the axis Ox and has coordinates $y$ and $z$ similarly permits a calculation of the ordinate Y of the center of gravity in a stage which is similar in design to the stage hereinabove described. As recalled earlier, the coordinate Z of the center of gravity can be calculated by means of either of the two sweeping beams.

Figure 3:
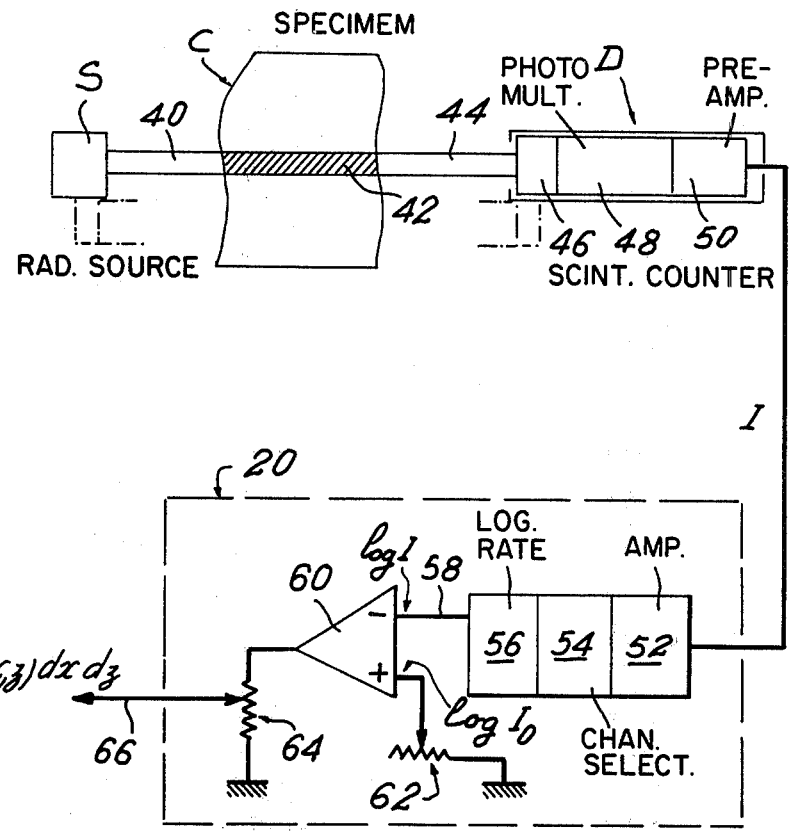
FIG. 3 is a diagram largely in circuit block form showing further detail regarding the detector and the unit 20 responsive thereto shown in FIG. 2.
Figure 4:
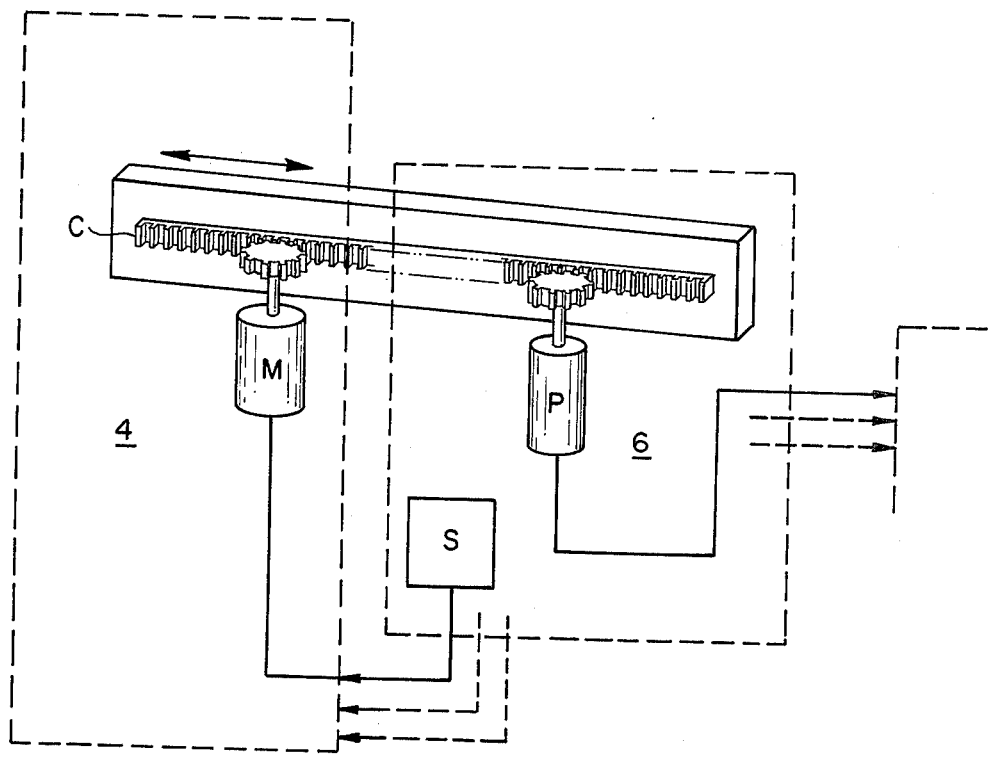
FIG. 4 is a diagrammatic representation of a well-known linear drive and position indicating means such as may be used for each of the coordinates of motion of the frame 3 of FIG. 1.

The schematic diagram of FIG. 3 illustrates one particular form of construction of the stage for calculating the mass of the unitary volume from a measurement of the intensity of the sweeping beam. In this figure, a source S emits a gamma radiation 40 having an intensity $I_0$ which passes through the object C in a unitary volume 42. The emergent ray 44 of intensity I impinges upon a scintillator 46 which is placed in front of a photomultiplier 48. A preamplifier 50 delivers at the output of the detector assembly D a signal which is proportional to I and which is amplified in the amplifier 52. An amplitude selector 54 transmits only those pulses delivered by the amplifier 52 which have an amplitude within a predetermined channel. A logarithmic ratemeter 56 counts the number of pulses located within the channel defined by the selector 54. The output 58 of the counting ratemeter 56 is connected to the negative input of an operational amplifier 60, the positive input of which is connected to ground through a potentiometer 62. The output of the operational amplifier 60 is connected to a potentiometer 64 which serves to adjust the output level of the assembly 20. The output 66 delivers a signal which is proportional to the mass $M(x,z).dx.dz$ of the unitary volume 42 through which the beam 40 passes.

In use of the device described in the foregoing takes place as follows: the determination of the mass of unitary volumes from the absorption of the sweeping beam presupposes a knowledge of the coefficient of absorption $a$. If the object or body to be studied is formed of a number of different substances, a difficulty can be introduced in the determination of the masses of unitary volumes if there are considerable differences between the coefficients of absorption of the various substances. On the other hand, this determination is easy if use is made of a monoenergetic radiation having an absorption which is substantially the same in the case of the different materials which constitute the body to be studied. These sources can be constituted by gamma emitters such as baryum-133, caesium-137, cobalt-60 or any X or gamma source having an energy of radiation within the band in which the absorption is substantially the same in the different substances of the body to be studied. The channel selected by the selector 54 of FIG. 3 is accordingly adjusted as a function of the energy range of the incident radiation 40 within which the absorption coefficient is substantially the same in the case of the different substances. Researches carried out by the present inventors have shown that a range of this type does exist, in particular in the case of human tissues.

When the detector D is in direct view of the source S, the potentiometer 62 is adjusted so that the output 66 of the stage 20 does not deliver any voltage. This means in other words that the voltage applied to the positive terminal of the operational amplifier 60 is equal to log ($I_0$). Under normal operating conditions, when an object C is interposed between the source and the detector, there is obtained at the output 66 a signal which is proportional to log ($I_0$) − log (I), that is to say in the final analysis and to within the nearest coefficient $a$ a signal which is proportional to the mass of the unitary volume 42 through which the analytical beam passes, thereby achieving the result which was announced.

What we claim is:

1. A device for determining the mass and the position of the center of gravity of an object comprising:
   at least one source of electromagnetic radiation which emits a beam of said radiation in a first predetermined direction, said first direction being the same for each source in the case of plural sources, and a corresponding number of detectors which serve to detect said radiation and each of which receives one of said beams,
   at least one source of electromagnetic radiation which emits a beam of said radiation in a second predetermined direction substantially perpendicular to said first predetermined direction,
   a movable support frame rigidly fixed to and mounting all of said sources and said detectors,
   means for moving said support frame with reference to a fixed base and with reference to said object linearly in at least two mutually perpendicular directions in such a manner as to cause said beams to scan all of said object,
   a system for determining the coordinates of the sources with respect to a reference trihedron during the scanning operation of said frame moving means, and
   calculating means comprising on the one hand stages for calculating the logarithm of the respective ratios between the intensity $I_0$ received by each detector when said detector is in inobstructed view of the source and the intensity I received by the same detector when the object is interposed between the source and the detector and, on the other hand, an assembly for calculating the coordinates of the center of gravity of the object, said calculating assembly being connected to and responsive to the outputs of said system for the determination of coordinates and to the outputs of said calculating stages.

2. A device according to claim 1, wherein said movable support frame is capable of displacement in the two directions respectively corresponding to said first and second predetermined directions and in a third direction at right angles to a plane defined by said first and second predetermined directions.

3. A device according to claim 1, wherein said calculating stages comprise in each case, successively, an amplifier connected to the output of the detector, an amplitude selector for transmitting only those pulses delivered by the amplifier which have an amplitude within a predetermined amplitude interval, a logarithmic ratemeter which counts the logarithm of the number of pulses having amplitudes within said interval, and an operational amplifier whose inverting input is connected to the output of the counting ratemeter and whose noninverting input is connected to ground through a resistance so adjusted that the output signal of said operational amplifier is zero when the detector is in unobstructed view of the source.

* * * * *

UNITED STATES PATENT AND TRADEMARK OFFICE
CERTIFICATE OF CORRECTION

PATENT NO. : 3,983,368
DATED : SEPTEMBER 28, 1976
INVENTOR(S) : Etienne CSAKVARY ET AL.

It is certified that error appears in the above-identified patent and that said Letters Patent are hereby corrected as shown below:

On the first page of the patent, line 1 of the abstract, change "A line body" to -- A live body --.

Signed and Sealed this

Twenty-ninth Day of March 1977

[SEAL]

Attest:

RUTH C. MASON
*Attesting Officer*

C. MARSHALL DANN
*Commissioner of Patents and Trademarks*